(12) United States Patent
Franz et al.

(10) Patent No.: US 8,648,707 B2
(45) Date of Patent: Feb. 11, 2014

(54) PROCESS FOR GENERATING AN ALARM, CONTROL DEVICE AND DEVICE FOR CARRYING OUT THE PROCESS

(75) Inventors: Frank Franz, Lübeck (DE); Michael Imhoff, Dortmund (DE); Matthias Göpfert, Hamburg (DE)

(73) Assignee: Dräger Medical GmbH, Lübeck (DE)

( * ) Notice: Subject to any disclaimer, the term of this patent is extended or adjusted under 35 U.S.C. 154(b) by 487 days.

(21) Appl. No.: 12/887,735

(22) Filed: Sep. 22, 2010

(65) Prior Publication Data

US 2011/0068929 A1    Mar. 24, 2011

(30) Foreign Application Priority Data

Sep. 23, 2009   (EP) ..................... 09171128

(51) Int. Cl.
*G08B 29/00* (2006.01)

(52) U.S. Cl.
USPC ............... 340/511; 340/573.1; 340/539.12

(58) Field of Classification Search
USPC ................. 340/539.12, 573.1, 511, 506
See application file for complete search history.

(56) References Cited

U.S. PATENT DOCUMENTS

| 2002/0035315 | A1* | 3/2002 | Ali et al. ............... 600/300 |
| 2004/0133087 | A1* | 7/2004 | Ali et al. ............... 600/323 |
| 2005/0033128 | A1* | 2/2005 | Ali et al. ............... 600/323 |
| 2006/0195025 | A1* | 8/2006 | Ali et al. ............... 600/323 |
| 2008/0208026 | A1  | 8/2008 | Noujaim et al. |
| 2012/0041316 | A1* | 2/2012 | Al Ali et al. ........... 600/479 |

FOREIGN PATENT DOCUMENTS

| DE | 199 46 980    | 4/2000 |
| EP | 0 540 144 A1  | 5/1993 |

* cited by examiner

*Primary Examiner* — Travis Hunnings
(74) *Attorney, Agent, or Firm* — McGlew and Tuttle, P.C.

(57) ABSTRACT

A process is provided for generating an alarm if at least one monitored parameter (13) deviates from at least one preset value or value range, with the detection or determination of parameter (13) in case of its deviation. The process takes into account a verification interval (25) of limited duration in time and with adaptation of the time limitation of the verification interval (25) as a function of the extent of deviation of parameter (13) from the preset value or value range. A control device, a device for generating an alarm, a treatment devices, a digital storage medium, a computer program product as well as to a computer program are provided.

24 Claims, 2 Drawing Sheets

PROCESS FOR GENERATING AN ALARM, CONTROL DEVICE AND DEVICE FOR CARRYING OUT THE PROCESS

CROSS REFERENCE TO RELATED APPLICATIONS

This application claims the benefit of priority under 35 U.S.C. §119 of European Patent Application EP 09 171 128.3 filed Sep. 23, 2009, the entire contents of which are incorporated herein by reference.

FIELD OF THE INVENTION

The present invention pertains to a process for generating an alarm, a control device, a device for generating an alarm, a treatment device, a digital storage medium, a computer program product as well as to a computer program.

BACKGROUND OF THE INVENTION

The monitoring of measured values or parameters and the generation of alarms in critical situations is standard.

SUMMARY OF THE INVENTION

One object of the present invention is to provide another process for generating an alarm if a parameter being monitored deviates from preset ("normal") values or value ranges.

The process according to the present invention comprises the detection or determination of the parameter in case of a deviation thereof over a verification interval of limited duration in time. A length of the verification interval is adapted, set or determined depending on the extent of deviation of the parameter from the preset values or value ranges.

The use of the expression "may be" or "may have," etc., in all the following explanations is to be considered to be synonymous to "preferably is" or "preferably has," etc.

The terms "value" and "value range" are used synonymously or interchangeably below.

The use of the singular form in connection with the designations "parameter," "measured value," "value" or "value range" is to be considered to be equivalent to the plural form and vice versa, because the presence or detection of an individual variable or of a plurality of these variables may be involved within the framework of the present invention.

The term "parameter" or "measured value" as it is being used here designates a variable or measured variable or characteristic or an expression thereof, which shall be used to make a statement on a expectable state or a change thereof. The variable may be a characteristic variable. It may be a variable derived from a measured variable. A plurality of parameters or measured values or one or more variables derived therefrom may be monitored. Dependences of individual parameters or measured values on one another may be monitored with the process according to the present invention as well. Examples of parameters or measured values monitored by means of the process according to the present invention include physiological parameters, especially vital parameters such as heart beat, breathing, temperature, etc., of a patient. They also include pathological signal patterns, e.g., arrhythmia analysis in the ECG.

The measured variables being monitored include, furthermore, measured values of analytical methods, environmental analysis or measured variables of process monitoring and the like. Even though the present invention will be described below essentially with reference to physiological or pathological parameters or variables, the present invention is not limited to an application in the field of medical or medical engineering processes. The present invention is rather applicable to all embodiments or designs in which parameters or measured values are monitored.

The term "deviation" as it is being used here designates that the parameter is above or below a preset value or value range. The deviation may be defined as the beginning of overshooting or undershooting. It may also be defined as a point in time at which the first deflection of the parameter that was on this side of the preset value over a period of time reaches its maximum on the other side of the value or combinations thereof. In addition, the deviation may also be defined as a change in the dynamics of the value pattern. This may be manifested, for example, in the form of a significant change in the rise or in the variance of the value pattern. Other possibilities of defining the deviation, which are known to the person skilled in the art, are likewise covered by the present invention.

"Values or value ranges" (hereinafter also called normal values or value ranges) may be defined as values or value ranges that prevail under usual conditions or are understood to be a normal range or a range that is not considered by the person skilled in the art to require or be worthy of an alarm. Such values or value ranges may be arbitrarily preset values or value ranges. They may be based on detected measured values (detected already prior to the concrete monitoring) or on empirical values. Such values or value ranges may be supported by a broad empirical basis; however, they may also have been determined in a case-specific manner (e.g., for a certain patient) or may have been set as normal values or ranges.

If the parameter to be monitored is in the range of normal values or within a normal value range, there is by definition no reason for action or intervention.

A "patient" in the sense of the present invention may be a human being or an animal. The patient may be ill or healthy. The patient may or may not require medical treatment.

A "detection or determination of the parameter" may involve a measurement of the parameter or measured value to be monitored. It is also possible to measure a measured variable associated with the parameter or measured value and to convert this into the desired parameter to be monitored.

The parameter may be detected continuously or at discrete time intervals or at certain points in time or at certain time intervals.

To make it possible to determine a deviation of the parameter from preset values or value ranges, on the one hand, but to keep the probability of possible false alarms low, on the other hand, provisions are made according to the present invention for detecting the parameter over a verification interval of a limited duration. If the parameter being monitored will again assume normal values within the verification interval, i.e., if the actual values do not overshoot or undershoot the threshold value within the verification interval and/or the parameter does not deviate from preset values or value ranges any longer, this short-term deviation is considered to be a freak value, which shall not have any consequences. As a consequence of this definition, no alarm will be triggered in such a case in an embodiment according to the present invention.

The term "verification interval of limited duration" as it is being used here may be defined as a time interval that follows the point in time of the deviation of the parameter or that begins at this point in time. Provisions are made according to the present invention for setting the length or duration of the verification interval as a function of the extent of the deviation of the parameter from the preset values or value ranges or for setting it as a value that can be varied or as a variable value.

A first threshold value or threshold value range and a second threshold value or threshold value range is set in one embodiment of the process according to the present invention. The first threshold value may be, for example, an upper threshold value or threshold value range, which corresponds to a maximum upper degree of danger to the patient or for the process being monitored. Analogously to this, the first threshold value may, of course, likewise be—also additionally—a lower threshold value or threshold value range. The terms "threshold value" or "threshold value range" as they are being used here designate a limit value or limit value range of the parameter or measured value whose overshooting or undershooting is accompanied by making a determination or the taking or termination of a measure.

A degree of danger—or a criticality—may reflect the severity or consequence of the deviation of the parameter from normal values or value ranges for the process being monitored, above all, of course, for a patient being monitored.

Additional medium threshold values or threshold value ranges between the upper threshold value or threshold value range and the preset value or value range—and/or between the lower threshold value or threshold value range and the preset value or value range—are determined or set in another embodiment of the process according to the present invention in order to represent different degrees of danger.

The term "medium threshold value or threshold value range" designates a value or value range of a medium danger potential deviating from the normal values or value ranges.

One or more such medium threshold values or threshold value ranges (hereinafter also called summarily threshold value) may be set or determined. The medium threshold values may be set at equally distributed distances or with fixed value distances between the upper or lower limit value and the normal value or value range. The distances of the medium threshold values from one another or from the upper and/or lower limit value may be determined arbitrarily or as a function of the changing danger potential. The latter may increase, e.g., linearly or nonlinearly, for example, exponentially. The distances between the threshold values may therefore be nonuniform.

Each value, each threshold value, but especially the additional medium threshold values may be based on empirical values and/or determined on the basis of data of a knowledge base that was available prior to the beginning of monitoring.

However, these values may also be set on the basis of monitoring values determined during the monitoring. They may be set automatically. The setting may also take place repeatedly. In particular, correction of the setting may be performed.

The term "empirical value" as it is being used here designates a value that can be derived from a personal and/or collective experience, for example, a value that was recognized as typical by clinical staff. An empirical value may be a value applicable to a target group of patients or to a concrete patient. For example, it is usually assumed that the heart rate (HR) of a healthy newborn at rest differs from that of a healthy 70-year-old person. If certain physical or psychological states are present, the empirical values may, in turn, deviate herefrom.

The term "knowledge base" as it is being used here designates a knowledge data bank that is used to collect information, for example, parameters, measured values or patterns, i.e., changes in the parameters or measured values over time. The knowledge base may have or contain parameter- and/or patient group-specific values for a certain parameter or measured value or an expression thereof. The knowledge base may comprise empirical values as described above.

A control device, such as a microprocessor, may be used for the automatic determination of the medium threshold values on the basis of the data being stored in the knowledge base.

Threshold values may be set automatically in various ways in the process according to the present invention.

In one embodiment of the process according to the present invention, a first threshold value is set as the lowest degree of danger and a second threshold value is determined as the highest degree of danger on the basis of data of the knowledge base.

The first threshold value may be a value or value range provided by a user (physicians, nursing staff, etc.). It may be based on empirical values. It may reflect the result of an actual measurement on a patient. It may be an arbitrarily set value.

The user may input values by means of an interface intended for that purpose, e.g., via a keyboard, into a control device, such as a microprocessor. The second threshold value may be a parameter- and/or patient group-specific threshold value.

The highest degree of danger preset by the second threshold value may be an emergency threshold value. The term "emergency threshold value" designates a value of a parameter or of a measured value at which, when reached, emergency measures are to be taken immediately.

Based on the first threshold value set by the user and a parameter- and/or patient group-specific emergency threshold value as a second threshold value, which is stored in the knowledge base and can be retrieved therefrom, the microprocessor determines or calculates, for example, by interpolation, n intermediate positions or medium threshold values (where n may be a natural integer).

In another embodiment, a first threshold value is set by a user as the highest degree of danger and medium threshold values and a lower threshold value are determined or calculated on the basis of data of the knowledge base.

Based on the threshold value set by the user and optionally based on information on the parameter to be monitored, for example, mean value and/or variance within the last 5 minutes, n patient-specific thresholds can be automatically determined by the microprocessor. In a case in which no history of the parameter to be monitored is available, normal values being stored in the knowledge base or normal values or value ranges can be used at first to set one, more or all thresholds or limit values.

The threshold value input by the user may correspond to the highest degree of danger, and the further threshold values or threshold value ranges (i.e., medium threshold values and lower threshold value) may correspond to lower degrees of danger.

A specific verification interval is assigned to a specific danger potential in another embodiment.

The term "specific verification interval" designates a verification interval with a certain length of the verification interval, whose duration is limited. The length of the verification interval preferably decreases with increasing degree of danger. The defined length of the verification interval for the lowest degree of danger preferably corresponds to the maximum possible delay of an alarm when the corresponding threshold value or threshold value range is slightly exceeded. By contrast, an alarm can be generated very rapidly in this manner in case of great deviations of the parameter from the preset normal values or value ranges. The specific length of the verification interval can be assigned to a specific degree of danger on the basis of data of the knowledge base. The length of the verification interval to which a certain degree of danger is assigned may be a parameter- and/or patient group-specific value. The value may be stored correspondingly in the knowledge base of the system, for example, in a memory.

Provisions are made in one embodiment of the process according to the present invention for determining the degree of danger on the basis of data of the parameter or of the measured value of a majority of patients or test subjects. The generalized data may then be extrapolated to an individual patient.

As an alternative to this, the assignment may be performed in a situation-specific manner on the basis of the stability or instability and/or "criticality" of the state of a patient.

The values for the length of the verification interval may be scaled in a situation-specific manner. For example, a shortening of the verification intervals in case of unstable patients may advantageously lead to more sensitive alarms in the sense of earlier alarms.

To automate scaling, it is possible in many areas, such as in medicine, to use so-called "scores," which provide information on the stability/criticality, e.g., the state of the patient.

It may be advantageously possible in this case to adapt the length of the verification interval individually (also) to the needs of a concrete (particular actual) patient. It may thus, in turn, be advantageously possible to further optimize the monitoring of a patient.

Provisions are made in another embodiment of the process according to the present invention for recording at least one time interval, in which the parameter deviates from the preset normal values or value ranges by more than a first threshold value or a threshold value range.

The recording of the time interval may take place in a suitable manner automatically or in an automated manner. Suitable means may be provided for this.

Results of the recording are preferably stored in a suitable memory device.

The duration of the time interval of the deviation may be measured and recorded in units of time. Depending on the application of the process, suitable units of time may comprise, e.g., μsec, sec, minute or hour. A counter may be used to detect and/or record the units of time.

The term "counter" as it is being used here designates a means that is suitable for detecting and possibly displaying the duration of the time interval. The counter may be an electronic counter. It may be a meter, which is designed to count continuous variables. Depending on the needs or accuracy and situation, the counter may be designed to detect units of time in integer units of time, for example, 1 sec, 2 sec, 4 sec, 10 sec, 20 sec, 50 sec, or in any designed fractions of such units of time. The counter may be designed to be able to switch between different units of time. The counter may be integrated in a control device or form part of such a control device. It may be able to be connected or be connected to a control device via suitable connections, such as lines, interfaces and the like. A single counter may be provided to detect the duration of the time interval of the deviation of the parameter from the preset normal values or value ranges, which deviation takes place as a whole. A plurality of counters of identical design or of different designs may be provided to detect the duration of the time interval of the deviation of the parameter from one value to another, e.g., next higher or lower value. For example, a first counter may be provided for detecting the duration of the time interval of the deviation of the parameter from the preset normal values or value ranges. A second counter may be provided for detecting the duration of the time interval of the deviation of the parameter from a medium threshold value. A third counter may be provided for detecting the duration of the time interval of the deviation of the parameter from an upper or lower threshold value or threshold value range, optionally of the emergency threshold value. Additional counters are possible.

In another embodiment of the process according to the present invention, the counter remains set to zero until the parameter deviates from the preset normal values by more than a first threshold value.

Provisions are correspondingly made in such an embodiment of the process according to the present invention for the counter to begin counting only when the parameter deviates from the normal values. If a plurality of counters are provided, it may correspondingly be possible for a first counter, which detects the duration of the time interval of the deviation of the parameter from the preset normal values or value ranges, to begin counting already while a second or third counter is still set to zero.

Provisions are made in another embodiment of the process according to the present invention for triggering an alarm signal when the parameter deviates from the preset normal values by more than a first threshold value over the time limit of the verification interval. More precisely, this means that the duration of the time interval of the deviation is greater than the time limit of the verification interval.

In another embodiment of the process according to the present invention, the counter is decremented (by, e.g., a unit of time) when the parameter drops to a value below a threshold value relevant for the counter over the duration of a unit of time and the value of the counter is greater than zero. The length or duration of the time interval of the deviation of the parameter can thus be reduced. Such a procedure may be especially advantageous in case of parameters alternating or fluctuating around a certain value or value range. Such a decrement function may advantageously contribute to guaranteeing prompt alarming even in case of alternating or fluctuating measured values. If the parameter again deviates beyond the threshold value or threshold value range (these two terms are summarily also designated threshold value here), the counter begins to run, and the units of time that correspond to the duration of the repeated deviation of the parameter are added to the current reading of the counter. It can thus be advantageously ensured that a critical deviation of the parameter can be detected with certainty despite the alternating or fluctuating pattern of the parameter.

No alarm signal is triggered as long as the units of time of the deviation of the parameter which are counted by the counter are smaller than the verification interval because the pattern of the parameter or the deviation of said parameter from the normal values or value ranges can be considered to be noncritical. If, by contrast, the units of time counted by the counter exceed the duration of the verification interval determined as a function of the degree of danger, an alarm signal is triggered in this embodiment.

The process according to the present invention is aimed at adapting the length of the verification interval to the degree of danger determined by the extent by which the threshold value is exceeded. Not only the mere violation of the threshold value over a short period of time, but also the extent and duration of the limit value violation are advantageously taken into account here.

The object of the present invention is likewise accomplished by a control device according to the present invention. All advantages of the process according to the present invention can also be achieved in full measure with the control device according to the present invention. The control device according to the present invention is configured or designed and/or provided for carrying out the process according to the present invention in full or in some of its steps. The control device according to the present invention may be a computer-assisted control device, such as a microprocessor, a CPU and the like. The control device may be integrated or is integrated in a computer. The control device may have suitable means for communication with other means, such as user interfaces and the like. The control device according to the present invention is preferably designed to process the detected parameters or measured values to be monitored. The control device may be designed to perform calculations and/or providing data for external interfaces. To store results, the control device may be able to be connected or may be connected to at least one memory means or to a memory/reading means.

The control device may be provided for graphically and/or numerically displaying the detected parameters or measured values on the user interface. The control device may be able to be connected or may be connected for this purpose to at least one input means for inputting the preset normal values. The control device may receive inputs of a user, for example, preset values, from the user interface, analyze them and/or convert the results obtained into a corresponding behavior of the device. Furthermore, the control device may be provided for checking and updating the alarm status of all parameters to be monitored preferably continuously or continually.

To detect a duration of the time interval of the deviation of a parameter from preset normal values by more than a first threshold value, the control device may preferably have at least one counter. The control device may, furthermore, be provided for generating an alarm signal when needed, i.e., when a critical state emerges or begins, or to cause such an alarm signal to be generated.

The object according to the present invention is also accomplished by a device for generating an alarm according to the present invention. All advantages of the process according to the present invention can also be achieved in full measure with the device according to the present invention. The device for generating alarm according to the present invention has at least one detection means for detecting or determining the current expression of a parameter being monitored, at least one comparison means for comparing the detected (current) parameter to preset normal values or value ranges, and at least one control device according to the present invention. The term "detection means" as it is being used here designates a means that is suitable for detecting or measuring a parameter or a measured value.

The detection means may be a measuring and preprocessing unit or means. The detection means may be a sensor or connected to one or more sensors. Depending on the intended use of the device according to the present invention, suitable sensors include a great variety of embodiments, including sensors for detecting biological and/or physiological properties, such as biosignals (ECG, EEG, temperature) of patients; sensors for detecting chemical and/or physical properties, such as temperature sensors, pressure-measuring sensors, sensors for measuring concentrations or changes in concentrations and the like. The parameters or measured values detected by the detection means may be converted, when needed, into variables (mostly electric signals) that can be processed further. Suitable preprocessing means, such as amplifiers, A/D converters, filters and the like, may be provided and/or integrated in the detection means. Further parameters may be derived from the processed or preprocessed parameters or measured values, e.g., the heart rate from the ECG.

The term "comparison means" as it is being used here designates a means that is provided and designed for comparing the currently detected parameter or measured value with the preset normal values or value ranges. Examples of suitable comparison means include means that perform a subtraction of the currently detected parameter or measured value from the preset normal value or vice versa. Depending on the difference obtained from the subtraction operation, a threshold value violation by the parameter or measured value to be monitored can be inferred. The extent of threshold value violation beyond the duration of the verification interval may lead to the triggering of an alarm signal.

In another embodiment, the device according to the present invention has at least one alarm means for triggering an alarm signal. The alarm signal may be triggered by means of acoustic and/or visual expression. In addition or as an alternative (i.e., exclusively), the alarm signal may consist of a signal for ending or beginning an operation. Thus, the administration of a drug can be stopped or started in a recognized state of alarm. The terms "alarm" and "state of alarm" as they are being used here are not therefore limited according to the present invention to an optical or acoustic message.

In another embodiment, the device according to the present invention has at least one memory means or memory/reading means for storing results. The terms "memory means" or "memory/reading means" designate a memory or a storage medium, which is usually used to store and secure data or information. The control device may access the memory means or memory/reading means for reading and writing in certain embodiments. The access of the control device to the memory means may take place by means of suitable data connections and/or data terminals, such as data connections among users of cables or wireless data connections, e.g., SATA, IR, Bluetooth, WLAN and the like. The memory means or memory/reading means may be integrated within the control device in certain embodiments. It is likewise possible here or in addition to use an external memory means or memory/reading means.

Examples of integrated memory means or memory/reading means include RAM, ROM, EPROM and the like. Examples of external memory means or memory/reading means include diskettes, CD ROMs, CDs, CD-RWs (rewritable CDs), DVDs, memory chips, SD cards (SD memory cards), chip cards, USB sticks and the like.

The memory means or memory/reading means may have various areas or partitions for storing configuration data, knowledge bases, user settings, status variables and/or history stream. In certain embodiments of the device according to the present invention, the memory means or memory/reading means has at least one data bank or can be coupled with such a data bank. Data of a knowledge base are or can be preferably stored in the data bank.

In one variant, the device according to the present invention has at least one input means for inputting the preset values or value ranges. Examples of such input means include a keyboard, a mouse, a touch pad, a microphone, a scanner, a card reader and the like.

In one variant, the device according to the present invention has at least one output means for outputting results of the control device. The outputting of the data or information may be performed graphically, e.g., in the form of a three-dimensional image, and/or numerically, e.g., in the form of a numerical value. Suitable output means include a monitor, a PDA (personal digital assistant), a printer or plotter and the like.

The object according to the present invention is also accomplished by a treatment device according to the present invention. All advantages of the process according to the present invention can also be achieved in full measure with the treatment device according to the present invention. The treatment device according to the present invention has at least one control device according to the present invention or at least one device for generating alarm according to the present invention. According to one embodiment, the treatment device according to the present invention may be designed or provided for monitoring a state of a patient. For example, the treatment device may be designed to monitor the heart rate of a patient. The treatment device may be a treatment device used in the area of acute medicine, such as a respirator, an anesthesia apparatus or the like.

The object according to the present invention is also accomplished by a digital storage medium according to the present invention. All advantages of the process according to the present invention can also be accomplished in full measure with the digital storage medium according to the present invention. The digital storage medium, which is especially a diskette, a CD or a DVD, preferably has electrically readable control signals, which can cooperate with a programmable computer system such that a process according to the present invention is carried out.

The object according to the present invention is also accomplished by a computer program product according to the present invention. All advantages of the process according to the present invention can also be accomplished in full measure with the computer program product according to the present invention. The computer program product preferably has a program code stored on a machine-readable carrier for carrying out the process according to the present invention when the program product is running on a computer.

The term "machine-readable carrier" as it is being used here designates a carrier that contains data or information that can be interpreted by software and/or hardware. The carrier may be a data carrier, such as a diskette, CD, DVD and the like. The object according to the present invention is also accomplished by a computer program according to the present invention. All advantages of the process according to the present invention can also be accomplished in full measure with the computer program according to the present invention. The computer program has a program code for carrying out the process according to the present invention when the program is running on a computer.

The present invention advantageously provides a process as well as suitable means and devices with which alarm signals can be advantageously generated reliably and reproducibly if physiological variables to be monitored or parameters derived therefrom leave a preset range.

It can be advantageously ensured by means of the present invention that alarm signals occur only in case of a significant violation of threshold values or threshold value ranges. It may advantageously be possible in this manner to substantially reduce the number of false alarms generated. The process can be advantageously applied to different parameters and patient groups due to the flexible manner of determining the necessary degree of danger-specific threshold values or threshold value ranges and delay intervals.

Based on the verification intervals set in a degree of danger-specific manner, the process according to the present invention can advantageously contribute to reducing or eliminating the number of alarms that are not associated with a clinically relevant and possibly critical state of a patient.

False alarms in a medical context are caused mainly by artifacts in the measured physiological signal, which are brought about by motion, procedures performed by the staff or other external disturbances. The process according to the present invention may advantageously also contribute to avoiding such false-positive alarm signals or to reducing the frequency of their occurrence. The process according to the present invention can be advantageously applied to a plurality of processes with a high rate of false alarms caused by limit value alarming.

Since significantly fewer false alarms are produced with the use of the process according to the present invention, users can respond to alarm signals and the alarm event associated therewith more adequately.

The alarm safety advantageously made available by means of the process according to the present invention in exclusively actually critical states may have a favorable effect on the expectations of the users: The users can have confidence in the alarms generated by the process according to the present invention. Furthermore, patient safety can be advantageously increased in this manner; users will respond adequately based on the reliable alarm events.

Due to the reduction of false alarms, which can be advantageously achieved according to the present invention, the noise and stress level can be advantageously reduced in the area of application of the monitoring devices. The present invention can advantageously reduce the stress associated with a high number of alarms generated due to noise, stress and the additional work load. This may be beneficial, e.g., for a patient.

The process according to the present invention advantageously has a low complexity, so that the alarm generation advantageously becomes reproducible and transparent to the user. The confidence of and acceptance by the user can thus be advantageously strengthened. The present invention is advantageously based on a simple operating concept, which is based on existing concepts and empirical values of the users and can make do with few interactions on the part of the user.

Another advantage of the process according to the present invention may lie in its general applicability even to different physiological variables and different patient groups.

Furthermore, it is advantageously possible to apply the process according to the present invention in all areas that require the detection and monitoring of parameters or measured values and a corresponding output of alarm signals in real critical states. The process according to the present invention thus advantageously offers the possibility of generalization.

Since complicated calculations are done away with, the process being described especially saves resources, and the device being described can thus be designed with microprocessors that have a lower performance and hence are energy efficient. The present invention will be explained below as an example on the basis of the drawings attached, in which identical reference numbers designate identical or similar components. In the figures, some of which are greatly simplified, The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
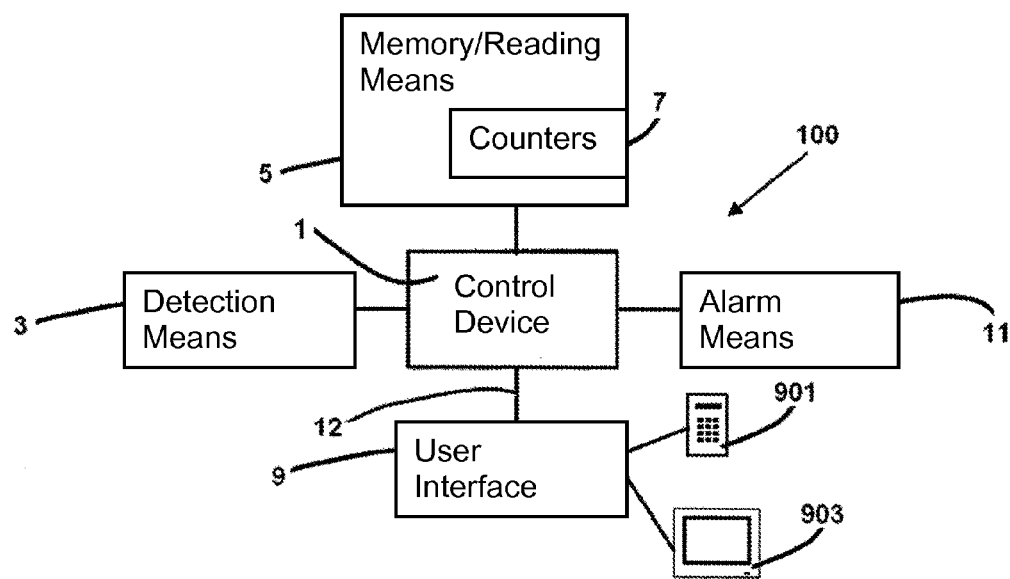
FIG. 1 is a schematic view showing a device according to the present invention.

Referring to the drawings in particular, FIG. 1 schematically shows a general view of components of a device 100 for generating alarm according to the present invention.

Device 100 for generating alarm has a control device 1, e.g., a microprocessor.

A control device 1 is connected to a detection means 3. Detection means 3 is provided for detecting or determining a parameter or measured value, which shall be monitored. Detection means 3 may be a sensor. The control device may include a comparison means for comparing the detected parameter (13) with preset values or value ranges.

Control device 1 is connected to a memory/reading means 5. The memory/reading means 5 may be a ROM or RAM. It may be an external memory/reading means, such as a diskette or CD.

Three counters 7, i.e., one for each threshold, are integrated in control device 1. Control device 1 could, however, also have any other number of counters.

The counters 7 are provided for detecting the particular duration of the time interval of the deviation of the parameter from the preset normal values or value ranges beyond a certain threshold value or threshold value range.

Control device 1 is connected to a user interface 9. User interface 9 may be connected to at least one input means 901 for inputting or storing parameters in the memory/reading means 5, e.g., a keyboard. User interface 9 may be connected to at least one output means 903 for outputting or displaying data, e.g., a monitor.

Control device 1 is connected, furthermore, to an alarm means 11. The alarm means 11 is provided for triggering an alarm, e.g., an acoustic alarm, if the parameter is above or below the normal value or value range beyond the length of a preset verification interval.

The individual components of the device 100 according to the present invention are connected to one another via a data line 12.

To carry out the process according to the present invention, a threshold value or threshold value range (preferably an upper threshold value or threshold value range and a lower threshold value or threshold value range in case of monitoring a value range) is set, for example, by a user via the user interface 9 for each parameter to be monitored.

Based on this threshold value or threshold value range and a knowledge base stored in the memory/reading means 5, additional thresholds can be automatically determined by means of control device 1. They may represent different degrees of danger. A corresponding verification interval length is assigned to each of these threshold values or threshold value ranges. The verification interval length preferably decreases with increasing degree of danger. Thus, the threshold value or threshold value range with the shortest verification interval may be violated in case of a very great rise of an actual value above the threshold value or threshold value range and an alarm may be sent, while the triggering of an alarm can be delayed during a slight overshooting only after the end of a longer verification interval.

During monitoring, control device 1 manages at least one counter 7, which represents the duration of the threshold value violation, in the memory/reading means 5 for each threshold value or threshold value range.

In the normal case, i.e., when the corresponding threshold value or threshold value range has not been exceeded by the particular parameter or measured value since a certain point in time, the value of counter 7 equals zero.

If the threshold value or threshold value range is now violated (i.e., overshot or undershot) by the currently detected parameter or measured value (output of the detection means 3), the duration of the particular threshold value violation is measured by the control device 1 and counter 7 in the memory/reading means 5 is correspondingly updated.

Furthermore, counter 7 can be continuously compared with the corresponding verification interval length—or with the number of units of time covered by same. If the violation continues, an alarm signal is generated by control device 1 and an alarm is triggered by means of alarm means 11.

If the parameter or measured value to be monitored does not violate the threshold value any longer, the corresponding counter 7 is not set back to zero immediately, but it counts backward.

One variant is a symmetrical decrement, in which case the corresponding counter 7 is minimized by one unit of time per unit of time without threshold value violation. This preferably happens as long as counter 7 does not assume the value zero or a repeated threshold value violation does not cause counter 7 to increase again. It can be advantageously ensured by this function that an alarm is sent in time even in case of values alternating around the threshold value or threshold value range.

Asymmetrical decrements may likewise also be provided according to the present invention.

Figure 2:
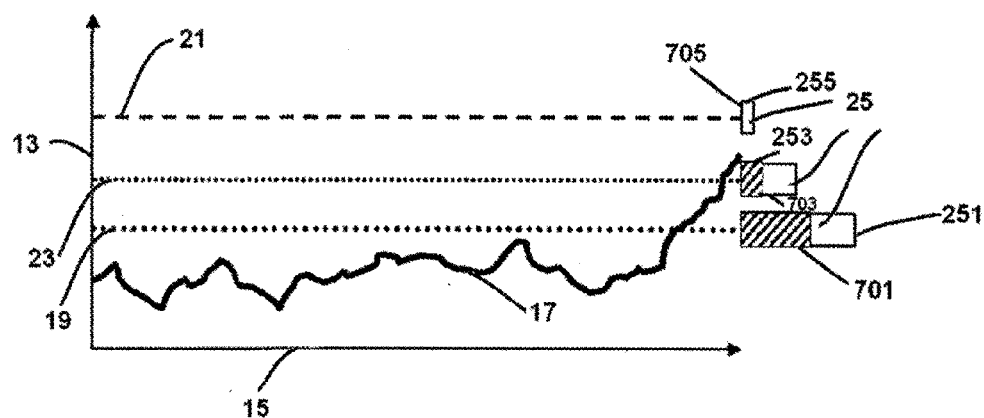
FIG. 2 is a graph for determining automatically generated threshold values or threshold value ranges according to a first alternative of the process according to the present invention.

FIG. 2 shows a graph for determining automatically generated threshold values according to a first alternative of the process according to the present invention.

The graph shows the pattern 17 of the parameter 13 to be monitored, which was plotted on the y axis, as a function of the time plotted on x axis 15, FIG. 2 shows an exemplary pattern 17 of the values of parameter 13 to be monitored.

According to the first alternative for determining the threshold values or threshold value ranges shown in FIG. 2, a user threshold value 19 is preset as a lowest degree of danger by a user.

A parameter- and/or patient-group-specific emergency threshold value 21 is determined based on data of a knowledge base.

Control device 1 calculates additional medium threshold values or threshold value ranges, e.g., by means of interpolation. FIG. 2 shows a single intermediate threshold or a single medium threshold value 23. As can be recognized in FIG. 2, the medium intermediate value 23 does not necessarily have to assume an averaged value between the user threshold value 19 and the emergency threshold value 23.

A specific verification interval 25 is assigned to each value or value range corresponding to the degree of danger, which is related to the extent of deviation of the parameter.

As can be clearly recognized in FIG. 2, a verification interval 251, which is assigned to the user threshold value 19, has a greater length or longer duration than a verification interval 253 of the medium threshold value 23 and even a verification interval 255 of the emergency threshold value 21. If a parameter 13 therefore violates the user threshold value 19, it will take longer until an alarm signal is triggered than when parameter 13 violates the emergency threshold value 21.

A counter 7, which detects the duration of the time interval of the deviation of the parameter or measured value from the preset normal value or value range, is associated with each value or value range. As soon as the value pattern 17 of the parameter 13 to be monitored exceeds a threshold value, the corresponding counter 7 begins to count or run, i.e., detect the duration of the threshold value violation in units of time.

Since the parameter 13 to be monitored has exceeded the user threshold value 19 and the medium threshold value 23 in the value pattern 17 shown in FIG. 2, the corresponding counters 701 and 703 are counting. However, since parameter 13 to be monitored has not yet exceeded or violated the thresholds longer than the corresponding respective verification intervals 251 and 253 (shaded area in verification interval 251 or 253 smaller than the overall duration of the verification interval), no alarm signal is triggered as yet.

Since, as is shown in FIG. 2, parameter 13 to be monitored does not (yet) exceed the emergency threshold value 21, counter 705 is still set to zero.

Figure 3:
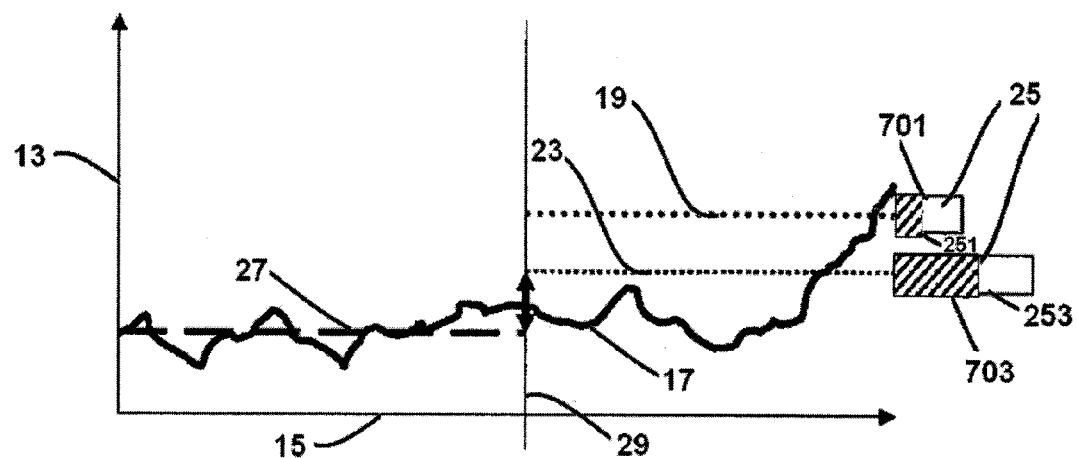
FIG. 3 is a graph for determining automatically generated threshold values or threshold value ranges according to a second alternative of the process according to the present invention.

FIG. 3 shows a graph for determining automatically generated threshold values or threshold value ranges according to a second alternative.

FIG. 3 shows an exemplary value pattern 17 of parameter 13 to be monitored, which corresponds—only for explanation purposes—to the value pattern shown in FIG. 2.

Patient-specific threshold values or threshold value ranges are automatically determined by the control device in the second alternative shown in FIG. 3 for determining the threshold values or threshold value ranges on the basis of a user threshold value 19 set by a user and on the basis of information on the parameter 13 to be monitored, e.g., a mean value 27 of the parameters or measured values over a past period of time.

Should no history of the parameter 13 to be monitored be available (not shown in FIG. 3), it would be possible at first to use normal values stored in the knowledge base to determine the threshold value ranges. The determination of the further threshold values or threshold value ranges, such as the medium threshold value range 23, may take place at a point in time 29 at which the threshold value is adapted.

In the procedure for determining the threshold value, which is described here, the user threshold value 19 may correspond to the highest degree of danger, and the medium threshold value 23 to a lower degree of danger.

An exemplary embodiment of the process according to the present invention for monitoring the heart rate (HR) will be described below with respect to maximum allowable values.

The possibility of extrapolation to other parameters and monitoring with respect to minimum allowable values (also lower limit values) is obvious. The first alternative for determining automatically generated threshold values or threshold value ranges, which was illustrated above with reference to FIG. 2, is used to determine the automatically generated thresholds and for the assignment of the verification interval lengths.

Reference is made to the reference numbers shown above in the drawings to explain the individual procedures.

A patient is connected in the initial situation to the detection means 3 of the alarm-generating device 100 via ECG electrodes in the exemplary embodiment being described here. Among other things, the processing of the raw ECG signals and the determination of the heart rate (HR) are carried out in detection means 3, which may be equipped as a measuring and preprocessing means.

The parameter- and/or patient group-specific values (HR) for the upper emergency threshold value 21 (for example, 180 beats per minute for an adult) as well as the verification interval lengths for all three thresholds (user threshold value 19 max.=60 sec, medium intermediate threshold value 23 max.=15 sec, emergency threshold value 21 max.=4 sec) are now loaded from the knowledge base stored in memory/reading means 5 at the beginning of monitoring.

Furthermore, the medium threshold value 23 is calculated on the basis of the current user threshold value 19 for HR max. as follows:

Medium threshold value=user threshold value+0.3*
(emergency threshold value−user threshold value).

If it is assumed, for example, that the user sets a user threshold value 19 of 120 beats per minute for HR max., a value of 138 beats per minute is obtained for the medium threshold value 23.

| Threshold | Source | Value | Length of verification interval |
|---|---|---|---|
| User threshold value | User | 120 beats per minute | 60 sec |
| Medium threshold value | Calculated | 138 beats per minute | 15 sec |
| Emergency threshold value | Knowledge base | 180 beats per minute | 4 sec |

In case of an adaptation of the user threshold value 19, the medium threshold value 23 may be recalculated, and all other parameters mentioned before may remain unchanged.

After this phase of initialization, control device 1 checks for each new value of the HR whether or not a threshold value or threshold value range is exceeded.

If HR rises above 120 beats per minute, counter 701 of the user threshold value 19 is increased by one unit of time. If HR has been higher than 120 beats per minute for the last 30 sec, the value of counter 701 consequently equals 30 sec.

Whenever a counter 7 changes, it is checked whether the numerical value is greater than the corresponding verification interval length. If so, a corresponding alarm signal is triggered by the alarm means 11.

If the value of HR drops again, for example, below 120 beats per minute, counters 7 are reduced for each unit of time below the corresponding threshold value or threshold value range. Consequently, if HR has the value of 100 beats per minute for 10 sec, value of counter 701 of the user threshold value 19 decreases again to 20 sec.

If HR now rises again, counters 7 are again increased correspondingly.

If HR increases, for example, abruptly from 100 beats per minute to 185 beats per minute, the counters 7 for all threshold values or threshold value ranges (user threshold value 19/medium threshold value 23/emergency threshold value 21) will count up, because the value violates all threshold values.

If HR is now 185 beats per minute longer than 4 sec, the value of counter 705 of the emergency threshold value 21 is greater than the corresponding verification interval length and an alarm signal is triggered. The state of counter 701 for the user threshold value 19 is 25 sec and the state of counter 703 for the medium threshold value 23 is 5 sec at this point in time. All counters 7 are reset to 0 sec after acknowledgment of the alarm by the user.

While specific embodiments of the invention have been described in detail to illustrate the application of the principles of the invention, it will be understood that the invention may be embodied otherwise without departing from such principles.

APPENDIX

LIST OF REFERENCE NUMBERS

| | |
|---|---|
| 100 | Device for generating alarm |
| 1 | Control device |
| 3 | Detection means |
| 5 | Memory/reading means |
| 7 | Counter |
| 701 | Counter of the user threshold value |
| 703 | Counter of the medium threshold value |
| 705 | Counter of the emergency threshold value |
| 9 | User interface |
| 901 | Input means |
| 903 | Output means |
| 11 | Alarm means |
| 12 | Data lines |
| 13 | Parameter |
| 15 | Time |
| 17 | Value pattern |
| 19 | User threshold value |
| 21 | Emergency threshold value |
| 23 | Medium threshold value |
| 25 | Verification interval |
| 27 | Mean value of the parameters/measured values |
| 29 | Point in time of threshold value adaptation |
| 251 | Verification interval of the user threshold value |
| 253 | Verification interval of the medium threshold value |
| 255 | Verification interval of the emergency threshold value |

What is claimed is:

1. A process for generating an alarm if at least one monitored parameter, representing a monitored state of a patient, deviates from at least one preset value or value range, the process comprising the steps of:
 detecting or determining a monitored parameter deviation from the preset value or value range over a verification interval, the verification interval having a time limitation of limited duration in time;
 adapting, setting or determining a length of the time limitation of the verification interval as a function of the parameter value; and
 generating an alarm when the parameter is at or above the preset value for the verification interval.

2. A process in accordance with claim 1, further comprising the steps of:
 setting a first upper or lower threshold value or a first threshold value range;
 upon a parameter overshooting or undershooting the set first upper or lower threshold value or first threshold value range, the beginning of a verification interval with a first duration is defined;
 setting a second upper or lower threshold value or a second threshold value range; and
 upon overshooting or undershooting the set second upper or lower threshold value or second threshold value range, the beginning of a verification interval of a second duration is defined, wherein the second duration is different from the first duration.

3. A process in accordance with claim 1, wherein at least one threshold value or threshold value range is determined on the basis of data of a knowledge base known before the beginning of the monitoring process and/or set automatically on the basis of at least one value determined during the ongoing monitoring process.

4. A process in accordance with claim 1, wherein at least one threshold value or threshold value range is determined on the basis of data of a knowledge base known before the beginning of the monitoring process and/or set on the basis of at least one value determined during the ongoing monitoring process.

5. A process in accordance with claim 1, wherein said at least one monitored parameter is a vital parameters of a patient.

6. A process in accordance with claim 1, further comprising:
 decrementing a counter if a parameter drops to a value below a threshold value relevant for the counter for the length of a unit of time and the value of the counter is greater than zero.

7. A control device for generating an alarm if at least one monitored parameter, representing a monitored state of the patient, deviates from at least one preset value or value range, the control device cooperating with a detecting means for detecting or determining a parameter and a memory or input providing preset parameter values or value ranges, the control device comprising:
 a comparison means for comparing the detected monitored parameter with preset values or value ranges;
 a verification interval monitor for monitoring a verification interval with a time limitation of limited duration in time; and
 a verification interval modifier for adapting, setting or determining a length of the time limitation of the verification interval as a function of the parameter value.

8. A control device in accordance with claim 7, wherein the control device:
 sets a first upper or lower threshold value or a first threshold value range;
 defines the beginning of a verification interval with a first duration defined upon a parameter overshooting or undershooting the set first upper or lower threshold value or first threshold value range;
 sets a second upper or lower threshold value or a second threshold value range; and
 defines the beginning of a verification interval with a second duration defined upon overshooting or undershooting the set second upper or lower threshold value or second threshold value range, wherein the second duration is different from the first duration.

9. A control device in accordance with claim 7, wherein at least one threshold value or threshold value range is determined on the basis of data of a knowledge base known before the beginning of the monitoring process and/or set automatically on the basis of at least one value determined during an ongoing monitoring process and/or set manually on the basis of at least one value determined during the ongoing monitoring process.

10. A control device in accordance with claim 7, further comprising:
 decrementing a counter if a parameter drops to a value below a threshold value relevant for the counter for the length of a unit of time and the value of the counter is greater than zero.

11. A device for generating an alarm if at least one monitored parameter of a patient deviates from preset normal values or value ranges, the device comprising:
 a detecting means for detecting or determining a monitored parameter representing a monitored state of the patient;
 a control device comprising a comparison means for comparing the detected parameter with preset values or value ranges, a verification interval monitor for monitoring a verification interval with a time limitation of limited duration in time and a verification interval modifier for adapting, setting or determining a length of the time limitation of the verification interval as a function of the parameter; and an alarm means for producing an optical or acoustic or a device function changing alarm upon the control device generating an alarm.

12. A device in accordance with claim 11, further comprising a memory means or memory/reading means for storing results.

13. A device in accordance with claim 11, further comprising an input means for inputting previously known values or value ranges.

14. A device in accordance with claim 11, further comprising at least one output means for outputting results of the control device.

15. A device in accordance with claim 11, wherein the control device:
- sets a first upper or lower threshold value or a first threshold value range;
- defines the beginning of a verification interval with a first duration defined upon a parameter overshooting or undershooting the set first upper or lower threshold value or first threshold value range;
- sets a second upper or lower threshold value or a second threshold value range; and
- defines the beginning of a verification interval with a second duration defined upon overshooting or undershooting the set second upper or lower threshold value or second threshold value range, wherein the second duration is different from the first duration.

16. A treatment device for monitoring a state of a patient, the treatment device comprising:
- a data input for input of preset parameter values or value ranges;
- a detecting means for detecting or determining a parameter representing a monitored state of the patient;
- a control device comprising a comparison means for comparing the detected parameter with preset values or value ranges, a verification interval monitor for monitoring a verification interval with a time limitation of limited duration in time and a verification interval modifier for adapting, setting or determining a length of the time limitation of the verification interval as a function of the value; and
- an alarm means for producing an optical or acoustic or a device function changing alarm upon the control device generating an alarm.

17. A treatment device in accordance with claim 16, wherein the control device:
- sets a first upper or lower threshold value or a first threshold value range;
- defines the beginning of a verification interval with a first duration defined upon a parameter overshooting or undershooting the set first upper or lower threshold value or first threshold value range;
- sets a second upper or lower threshold value or a second threshold value range; and
- defines the beginning of a verification interval with a second duration defined upon overshooting or undershooting the set second upper or lower threshold value or second threshold value range, wherein the second duration is different from the first duration.

18. A digital storage medium system including:
- a digital storage medium comprising at least one of a diskette, CD, DVD or digital readable medium;
- a programmable computer system providing an electrically readable control signal output based on data provided by the digital storage medium;
- a detecting means for detecting or determining a parameter based on monitoring a state of the patient;
- a control device comprising a comparison means for comparing the detected parameter with preset values or value ranges, a verification interval monitor for monitoring a verification interval with a time limitation of limited duration in time and a verification interval modifier for adapting, setting or determining a length of the time limitation of the verification interval as a function of the parameter value; and
- an alarm means for producing an optical or acoustic or a device function changing alarm upon the control device generating an alarm.

19. A digital storage medium system in accordance with claim 18, wherein the control device:
- sets a first upper or lower threshold value or a first threshold value range;
- defines the beginning of a verification interval with a first duration defined upon a parameter overshooting or undershooting the set first upper or lower threshold value or first threshold value range;
- sets a second upper or lower threshold value or a second threshold value range; and
- defines the beginning of a verification interval with a second duration defined upon overshooting or undershooting the set second upper or lower threshold value or second threshold value range, wherein the second duration is different from the first duration.

20. A computer program product with a non-transitory program code stored on a machine-readable carrier or a non-transitory computer program with program code for carrying out the process comprising the steps of generating an alarm if at least one monitored parameter, representing a monitored state of the patient, deviates from at least one preset value or value range comprising:
- detecting or determining a parameter deviation over a verification interval with a time limitation of limited duration in time; and
- adapting, setting or determining a length of the time limitation of the verification interval as a function of the parameter value.

21. A computer program product in accordance with claim 20, further comprising the steps of:
- setting a first upper or lower threshold value or a first threshold value range;
- upon a parameter overshooting or undershooting the set first upper or lower threshold value or first threshold value range, the beginning of a verification interval with a first duration is defined;
- setting a second upper or lower threshold value or a second threshold value range; and
- upon overshooting or undershooting the set second upper or lower threshold value or second threshold value range, the beginning of a verification interval of a second duration is defined, wherein the second duration is different from the first duration.

22. A computer program product in accordance with claim 20, wherein at least one threshold value or threshold value range is determined on the basis of data of a knowledge base known before the beginning of the monitoring process and/or set automatically on the basis of at least one value determined during the ongoing monitoring process.

23. A computer program product in accordance with claim 20, wherein at least one threshold value or threshold value range is determined on the basis of data of a knowledge base known before the beginning of the monitoring process and/or set automatically on the basis of at least one value determined during an ongoing monitoring process and/or set manually on the basis of at least one value determined during the ongoing monitoring process.

24. A computer program product in accordance with claim 20, further comprising:
    decrementing a counter if a parameter drops to a value below a threshold value relevant for the counter for the length of a unit of time and the value of the counter is greater than zero.

* * * * *